(12) United States Patent
Kolen et al.

(10) Patent No.: US 11,660,502 B2
(45) Date of Patent: May 30, 2023

(54) HEIGHT JUMPING SENSOR SYSTEM AND METHOD

(71) Applicants: Paul T. Kolen, Encinitas, CA (US); John Andrew Wells, Phoenix, AZ (US)

(72) Inventors: Paul T. Kolen, Encinitas, CA (US); John Andrew Wells, Phoenix, AZ (US)

(*) Notice: Subject to any disclaimer, the term of this patent is extended or adjusted under 35 U.S.C. 154(b) by 267 days.

(21) Appl. No.: 17/300,140

(22) Filed: Mar. 23, 2021

(65) Prior Publication Data

US 2022/0305337 A1 Sep. 29, 2022

(51) Int. Cl.
*A63B 24/00* (2006.01)
*A43B 5/00* (2022.01)
*A43B 3/34* (2022.01)

(52) U.S. Cl.
CPC ............ *A63B 24/0062* (2013.01); *A43B 3/34* (2022.01); *A43B 5/00* (2013.01); *A63B 2220/20* (2013.01);
(Continued)

(58) Field of Classification Search
CPC ............ A63B 24/0062; A63B 2220/20; A63B 2220/836; A63B 2225/02; A43B 3/34;
(Continued)

(56) References Cited

U.S. PATENT DOCUMENTS 4,089,057 A * 5/1978 Eriksson ................ G01B 11/02
702/158
5,031,903 A 7/1991 Clarke
(Continued)

FOREIGN PATENT DOCUMENTS

WO WO-2022183166 A1 * 9/2022

OTHER PUBLICATIONS https://www.ptdirect.com/training-delivery/client-assessment/vertical-jump-test-sargent-jump--2013-a -predictive-test-of-lower-limb-power, Vertical jmp Test (Sargent Jump)—PT Direct, Internet article, 2013, pp. 1-2, US.
(Continued)

*Primary Examiner* — Francis C Gray

(57) ABSTRACT

An athlete wearing footwear measures jump heights with a motion sensor mounted on the footwear over toes of the athlete. By sensing vertical jump start motions the sensor detects jump start and finish times of −4 g start and −4 g landing. The sensor, a body wearable mems sensor developed by JAWKU, L.L.C., has a previously installed generic factory scale calibration factor. The athlete replaces this calibration factor with a new calibration scale factor selecting an "absolute" external reference device which measures jump height. This device measures several jump heights then inputted to an algorithm app in the sensor to calculate the new calibration scale factor customized to the actual athlete. The motion sensor has built in programming apps to periodically receive an upgraded factory scale calibration factor which upgrade is based on an ever increasing data pool of jump heights. The updated factory calibration factor is then again replaced by the athlete personally taking several new measured jumps which jump heights are in turn inputted to the sensor. The progress made in evolving jumping skills based on training and specific conditioning exercises can thus be motion sensor evaluated.

15 Claims, 4 Drawing Sheets

(52) U.S. Cl.
CPC ..... *A63B 2220/836* (2013.01); *A63B 2225/02* (2013.01)

(58) Field of Classification Search
CPC .......... A43B 5/00; A43B 3/44; A61B 5/6895; A61B 2503/10; A61B 2505/09
See application file for complete search history.

(56) References Cited

U.S. PATENT DOCUMENTS

| | | | | |
|---|---|---|---|---|
| 5,844,861 | A * | 12/1998 | Maurer | A43B 3/00 368/110 |
| 6,181,647 | B1 * | 1/2001 | Tipton | A63B 5/16 368/110 |
| 8,253,586 | B1 * | 8/2012 | Matak | G06F 17/00 340/870.07 |
| 9,704,412 | B2 | 7/2017 | Wells et al. | |
| 9,855,484 | B1 * | 1/2018 | Matak | A61B 5/0022 |
| 2016/0219968 | A1 * | 8/2016 | Martin | A61B 5/6807 |
| 2016/0220867 | A1 * | 8/2016 | Flaherty | G16H 20/30 |
| 2020/0230486 | A1 * | 7/2020 | Shau | A63B 71/0622 |

OTHER PUBLICATIONS

"Adhesion and friction in gecko toe attachment and detachment", Proc Natl Acad Sci, USA, Dec. 19, 2006; 103(51):19320-19325, PMCID1748224; pp. 1-17 online Dec. 5, 2006. doi: 10.1073/pnas.060884110, PNID: 17148600. Yu Tian, Noshir Pesika, Hongbo Zeng, Kenny Rosenberg, Boxin Zhao, Patricia McGuiggan, Kellar Autumn, Jacob Israelachvili.

"Carbon nanotube-based synthetic gecko tapes", Proc. Natl Acad Sci, USA, Jun. 26, 2007; 104(26); 10792-10795. published online Jun. 10, 2007., pp. 1-19, doi: 10.1073/pnas.0703505104 Engineering, PMCD: PMC1904109, PMID: 17578915. Liehui Ge, Sunny Sethi, Lijie Ci, Puliket M. Ajayan, Ali Dhinojwala.

"Gecko tape will stick you to ceiling", Will Knight, newscientist.com/article/dn3785-gecko-tape-will-stick-you-to-ceiling/., pp. 1-3, Jun. 1, 2003.

* cited by examiner

HEIGHT JUMPING SENSOR SYSTEM AND METHOD

CROSS-REFERENCE TO RELATED APPLICATION/INCORPORATED BY REFERENCE

This application makes reference to and incorporates in its entirety Provisional Application 63/100,903, filed Apr. 8, 2020 and entitled "HEIGHT JUMPING SENSOR SYSTEM & METHOD". The present application also claims the priority date of Provisional Application 63/100,903.

FIELD OF THE INVENTION

The present invention relates to the accurate measurement of the height of a jump by an athlete wearing a universal motion exercising sensor mounted in a holder on footwear directly above the toes of the athlete.

BACKGROUND OF THE INVENTION

Prior art devices such as the universal motion sensor of JAWKU, L.L.C., a Delaware company, and disclosed in U.S. Pat. No. 9,704,412, entitled "Biometric Data Gathering", the disclosure of which is incorporated in its entirety, are known for measuring jumping height of an athlete using a 6-DOF (degrees of freedom) 3 axis accelerometer/3 axis gyroscope sensors. This type of motion sensor is known as a "mems" (miniature electrical mechanical system) sensor and can be mounted on or near the center of mass (CM) of the athlete's body such as the chest. When directly sensing the body CM motion by placing the sensor as near the body CM as possible, the skin/muscle motion about the CM induces an excessive amount of sensor noise generated by this motion relative to the body CM, i.e. muscle "rippling" as seen in slow motion video. This motion induces sensor signal noise preventing the sensor from determining the body CM motion with sufficient accuracy and repeatability to directly determine the jump height with the required high degree of accuracy. Placing the motion sensor on the ankle area also introduces unwanted motion noise affecting the accuracy and repeatability of the jump height being measured.

BRIEF SUMMARY OF THE INVENTION

This invention, as shown in the FIG. 1 graph, "Corrected Acceleration (in g)", shows −4 g/−4 g trigger points for the toe-mounted sensor. To achieve greater accuracy of the height jump estimate requires calibration to determine a scale factor $K_{CAL}$ using the "raw" delta T (time) between the takeoff −4 g data point and the landing −4 g data point. As shown by Graph 1, these points are easy to find within the sensor code itself due to being much greater in absolute value than the typical body induced noise. The delta T (time) is measured in milliseconds as shown in Graph 1. The takeoff and landing times are conveniently measured at the −4 g/−4 g takeoff and landing points for greatest delta T accuracy. The placement of the motion sensor securely over the toes of one foot (the dominant foot) of the athlete enhances clear jump start and jump landing signals easily detected by the motion sensor over the lower level of motion background noise.

It has been found that the delta T derived from the −4 g data points will always calculate a jump height considerably lower than the real jump height. The primary reason for this is due to the body not being a rigid body during the take-off stage of the jump. The toe-mounted sensor will not detect motion until the toes quickly accelerate off the ground. Other lesser factors unique to the particular athlete, such as the extent of bending of the athlete's knees and arm movements, also interfere with the motion sensor's accuracies in gathering the start and landing data points. However, as the toe-sensor is coupled to the foot motion, it cannot directly sense the acceleration associated with the body center of mass (CM). It was experimentally determined that the toe body location generates the lowest body induced noise due to being mechanically coupled to the ground preventing significant foot motion noise.

When the jump is initiated the body CM is already moving vertically well before the toes actually leave the ground, as detected by the takeoff −4 g data point via the toe-mounted sensor. This results in an unknown time delay between the "true" CM take-off data point and the −4 g data point.

Calibration is required to determine, and remove, the aforementioned delay from the jump height calculation. It has been determined that little to no significant time delay exists between the "true' body CM landing data point and the −4 g landing data point. This is due to the body being in full extension while in free fall. The full body extension effectively creates a quasi-rigid body resulting in the body CM and toe-mounted sensor experiencing the same acceleration.

DETAILED DESCRIPTION OF THE INVENTION

Figure 1:
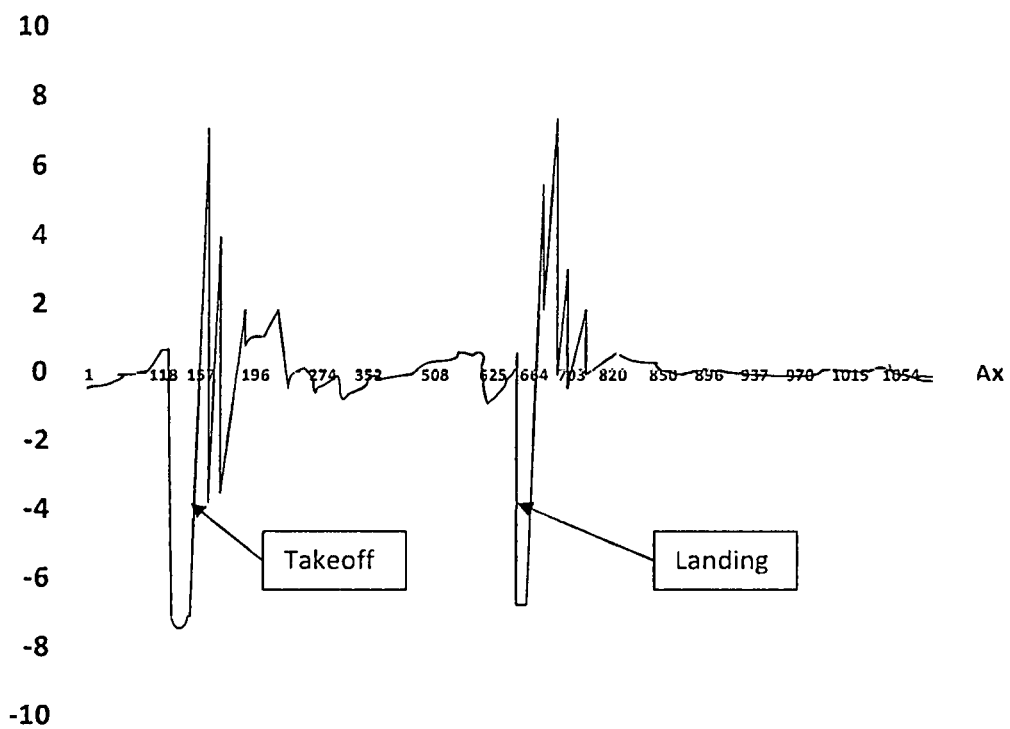
FIG. 1 is a Corrected Acceleration (in g) Graph of a jump depicting sensed jump time takeoff and landing data in milliseconds versus acceleration in g.

A motion calculating algorithm in the toe-mounted motion sensor has a generic factory loaded calibration scale factor or generic preloaded calibration scale factor for the −4 g takeoff data point time delay mentioned above. This factor is derived from the toe mounted motion sensor's data captured in hundreds of experimental jumps by different athletes each inherently having a very similar but still slightly unavoidable different body form (posture) jumping technique. This generic factory loaded calibration scale factor may be fine tuned by inputting several accurately measured jump heights to achieve a personalized "unique calibration scale factor" for the individual jumper which unique calibration scale factor replaces the generic factory loaded calibration scale factor. Also, the updated data from personalized jumps permits an ongoing refinement/upgrade of both the generic factory loaded calibration scale factor and the unique calibration scale factor for each jumper.

Two alternative calibration methods are proposed to allow the removal of the unknown delay:

1) External (Vertec®) Calibration:

This calibration is the simplest, relatively accurate, and widely available at training facilities. It requires the use of a Vertec® or similar direct jump height device, to be used as an "absolute" external reference. Basically, a Vertec device is one of the most common apparatus for measuring vertical jump heights. It is of steel frame construction with horizontal stacked marked measurement vanes which are rotated out of the way by the reaching hand of the athlete at the apex of the jump. An example of such device may be found in U.S. Pat. No. 5,031,903, entitled "VERTICAL JUMP TESTING DEVICE". However, the jumper during landing must not overly bend the knees or arm swing in an attempt to extend the air time of the jump.

This calibration procedure requires the jumper to determine the jump height from the external reference device and enter it into the calibration app. The calibration app has already been preloaded into the smartphone or smartpad or other mobile smart computer device of the athlete. During this calibration jump, the sensor is simultaneously determining the delta T between the −4 g/−4 g sensor points. Using the external reference jump height, entered manually, and the sensor −4 g/−4 g delta T derived jump height, yields a scale factor defined as $$K_{CAL} = \text{reference height/sensor height} = (H_{REF}/H_{SENSOR})_{CAL} \quad (1)$$

By taking a few calibration jumps, 4-8 attempts, an accurate scale factor $K_{CAL}$ can be determined for the individual jumper by a simple averaging of the $K_{CAL}$ associated with each calibration jump. Care must be taken to ensure the athlete is not fatigued by previous jumping prior to the calibration jumps. Once this scale factor is determined it is used to derive the "true" jump height from the sensor jump height via:

$$\text{Jump height} = H_{SENSOR} * K_{CAL} \quad (2)$$

Once the calibration is complete, the unique jumper $K_{CAL}$ will in the toe sensor replace the generic $K_{CAL}$ shipped with the app.

If an external jump height device is unavailable, a high-speed video camera method may be substituted.

2) External Video Calibration

It has been found that a video camera frame rate per second (fps) using a 5G or greater smartphone camera(s) or other mobile 5G smart computer device captures greater accuracy for calibration purposes and is preferred as an absolute external reference device.

Best examples of the smartphone used is a smartphone having an iOS 10 or higher or an Android™ equivalent operating system, such as Samsung Galaxy S10™ or higher series such as the Galaxy S20 or S21 series.

The camera of the smartphone is placed in a near vertical position within a few feet of the jumper's feet. The smartphone uses slow motion of at least (240 fps) video recording for each jump.

This method requires a known association between a reference jump height $H_{REF}$ (Vertec), jump height derived from the −4 g/−4 g sensor delta T, $H_{SENSOR}$, and the jump height determined by the slow-motion video, $H_{VIDEO}$.

All three of these parameters, $H_{REF}$, $H_{SENSOR}$, and $H_{VIDEO}$ are captured and saved for the same jump during the factory calibration. Multiple jumps can be averaged to reduce the effect of noise on the subsequent scale factors These three height measurements are used to create two factory scale factors, $K_{V-FACTORY}$ and $K_{S-FACTORY}$ defined as:

$$K_{V-FACTORY} = \text{reference height/video height} = (H_{REF}/H_{VIDEO})_{FACTORY} \quad (3)$$

and $$K_{S-FACTORY} = \text{reference height/sensor height} = (H_{REF}/H_{SENSOR})_{FACTORY} \quad (4)$$

With $K_{V-FACTORY}$ and $K_{S-FACTORY}$ determined, the reference height can be eliminated via $$R_{FACTORY} = (H_{REF}/H_{VIDEO})_{FACTORY}/(H_{REF}/H_{SENSOR})_{FACTORY} = (H_{SENSOR}/H_{VIDEO})_{FACTORY} \quad (5)$$

As seen, the reference height is eliminated, leaving only a simple scale factor between the video and sensor. It has been experimentally determined that even though the $H_{SENSOR}$ and $H_{VIDEO}$ will vary for a given $H_{REF}$ from jumper to jumper, the ratio remains extremely consistent.

This consistency allows the $R_{FACTORY}$ to be used to calibrate the individual jumpers $K_{S-JUMPER}$ via a simple video calibration without the need for a known external $H_{REF}$. The factory derived generic scale factors $H_{V-FACTORY}$, $H_{S-FACTORY}$ and $K_{S-FACTORY}$ are stored within the app as constants.

To calibrate the Individual Jumper sensor, the jumper will execute a jump while simultaneously using the toe-mount sensor and the high-speed video functions on a single smartphone. In this video calibration mode, a single sensor button touch will:

a) activate the sensor to begin searching for the −4 g/−4 g delta T, then send delta T to the app to be used to determine the $H_{SENSOR}$ for the current jump.

b) trigger the high-speed video capture, which begins at a signal such as a gunshot sound, and records for 4 seconds. The jumper will then post-analyze each video manually to determine the $H_{VIDEO}$ for the current jump.

Since both $H_{SENSOR}$ and $H_{VIDEO}$ were derived from the same jump, the following is true:

$$H = H_{SENSOR} * K_{S-JUMPER} = H_{VIDEO} * K_{V-JUMPER} \quad (6)$$

Additionally, due to the consistency of R, the following is also true $$R_{JUMPER} = R_{FACTORY} \quad (7)$$

Or $$(H_{SENSOR}/H_{VIDEO})_{JUMPER} = (H_{SENSOR}/H_{VIDEO})_{FACTORY} \quad (8)$$

By combining eqns. 2-8, the following relation is derived as:

$$K_{S-JUMPER} = K_{S-FACTORY} * (H_{SENSOR}/H_{VIDEO})_{JUMPER} * (H_{VIDEO}/H_{SENSOR})_{FACTORY} \quad (9)$$

With the now normalized $K_{S-JUMPER}$ determined for the individual jumper, the factory value is overwritten and subsequently used to determine the jump height H as $$H = K_{S-JUMPER} * H_{S-Jumper} \quad (10)$$

The jumper will execute 4-8 jumps, all stored to memory. After all calibration jumps have been executed and stored, the jumper will manually determine the $H_{V-JUMPER}$ for each stored video file. The video camera may, optionally, include an augmented reality height overlay grid for each frame to aid the manual determination of $H_{V-Jumper}$ height distance. The multiple $H_{V-JUMPER}$, and associated stored $H_{S-JUMPER}$, will allow averaging to reduce the effect of noise on the calculated $K_{S-JUMPER}$.

By experimentation it was found that the best method for recording the calibration video jumps was to position the phone in a near vertical orientation with the phone's camera aimed horizontally (landscape) or vertically (portrait) in a phone cradle no more than 1 meter from the jumpers' feet. This is helpful in keeping the jumper's feet and knee posture in frame, particularly when the jumpers' landing is off center. In the smartphones of the Galaxy® S20, S20+ and S20 Ultra and S21 Ultra series Hybrid Optic Zoom and/or Space Zoom captures view of complete jumper's body motions frame by frame.

It is also recommended that the video jump feature be retained even though it is only needed for the video calibration. By being able to record the jump, using the camera to take a selfie, the video can be uploaded to a website for later analysis by the jumper or trainer/coach. Like the art of swinging a golf club, correctly executed exercises and ideal body posture, (knees bending on takeoff and landing, arm movement, etc), may be further modified as required by specific exercises.

Finally, as the jumper database increases over time, the factory values will be "fine-tuned" given the ever larger population used in the statistics. Thus the database is a "living dynamic data base" fed by an ever increasing volume of vetted jump data. These updated factory constants will be included in subsequent app updates as required as will new calibration jump data in response to this changing data. Measuring vertical jump height with video yields the hang time defined as the difference between the smartphone app time stamp of the landing and the time stamp of the takeoff. This is possible because jump height is a known function of the time between take-off and landing (hang time). With the hang time ascertained, the toe mounted motion sensor app calculates the jump height using the earth surface acceleration as:

$$\text{Vertical jump height} = 0.5 \times (32.1850 \text{ ft/s}^s \text{ or } 9.81 \text{ m/s}^2) \times (\text{hang time}/2)^2$$

While accuracy can be obtained using a high video frame rate (240 fps) this approach has several faults, most important are the landing posture of the jumper's knees. Body posture during landing such as not having excess knee bending is considered crucial as landing with exaggerated bent knees increase a biased air-time resulting in a higher level of inconsistent jump time data.

The use of a generic factory preloaded video calibration factor placed in the motion sensor enables the athlete to select between the choice of an external height measuring Vertec device or an external higher end smartphone's video frame per second slow motion recording operating system. The athlete can easily switch between the two dependent on the availability of the equipment.

Figure 2:
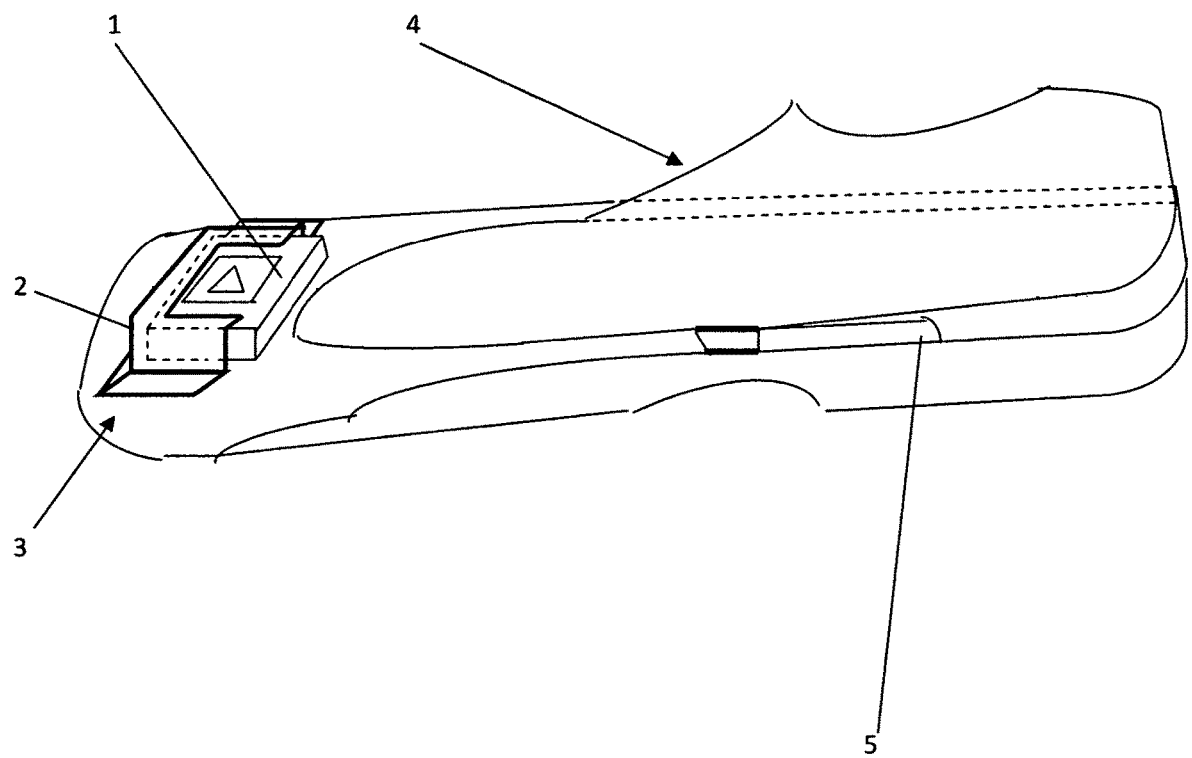
FIG. 2 is a perspective view showing a removable toe sock or slipper mounting a motion sensor in a holder strapped to an athlete's footwear with the sensor directly above the athlete's toes.

FIG. 2 shows a removable motion sensor 1 inserted in holder 2 above the toes of the athlete. The holder is mounted to a flexible outer slipper (toe sock) 3 which in turn is removable and also securable to the shoe 4 by a strap 5. The holder has three sides forming a "U" to snugly contact the motion sensor with a fourth side open to permit ease of motion sensor placement and removal. At least two of the three sides have an overhang portion directly above a top surface of the motion sensor to prevent upward dislodgment during jumping by the athlete. Operation of the motion sensor with a touch of a button on the sensor by the athlete causes a 2-4 second delay before an audible sound, such as a gunshot, signals the simultaneous start of the jump and the timing of the hang time by the motion sensor or the video recording if the smartphone is the external reference device.

A range of toe sock foot sizes are employed to fit the right or left foot to allow customized fit of the dominant left or right foot for different athletes.

The motion sensor 1 is in modular form and is the same as the sensor worn on the wrist of the athlete as disclosed in the U.S. Pat. No. 9,704,412. Motion detecting algorithms specific to detecting the start time and finish time of a vertical jump are downloaded to the motion sensor.

In a variation (not shown), a first magnet is mounted to the outer bottom of the holder to magnetically couple with a second magnet in the form of a metal segmented strip or disc on the outer or inner surface of the flexible slipper. The first and second magnets are thin and formed as "mirror" images.

In another variation (not shown), the slipper 3 is not used and instead first and second thin mirror image magnets are mounted, one directly to and beneath the holder 2 with the second thin magnet mounted to the shoe. The second magnet is mounted on either the outer surface or the inner surface of the shoe above the toe area to complete a magnetic coupling. It is very important for purposes of vertical motion sensor accuracy that the magnets hold the holder in snug contact with the toe area to minimize holder movement relative to the toes. To ensure foot comfort of the athlete, it is preferred that the second magnet be as thin as practical. A thin segmented magnetic band rather than a disc is useful in spreading out the magnetic surface. The magnetic coupling has the advantage of not requiring a left or right foot version unlike the slipper version previously discussed.

Another inexpensive interlock device (not shown) suitable to hold the bottom surface of the holder 2 to the top surface of the footwear are two part Velcro® tape pads of the hook and loop type. These pads require each pad having a thin adhesive backing.

A preferable interlock device suitable in place of the Velcro® tape pads is a releasable "Gecko". tape precut into pads secured by way of example by an adhesive layer on ONLY the undersurface of the sensor holder 2.

The reference to "releasable" refers only to the interlock between the holder and the outer surface of the footwear worn by the athlete. Application of hand pressure to effect securing and removal is all that is needed to effect interlock and release of the holding force of the "Gecko" tape. A commercial Geckskin® tape is an example of a suitable gecko tape. The Geckskin® tape eliminates the need for a Velcro pad two-part interlock requiring each pad to have adhesive on the back side of the pad.

The term "Gecko tape" refers to a NONADHESIVE or DRYADHESIVE surface force referred to in the scientific literature as a "dry adhesion force" in the article from the Proceedings of the National Academy of Science entitled "Adhesion and friction in gecko toe attachment and detachment" (the citation is: Proc Natl Acad Sci USA. 2006 Dec. 19; 103(51): 19320-19325), PMCID1748224. This was published online 2006 Dec. 5. doi: 10.1073/pnas.060884110, PNID: 17148600. These two articles are incorporated by reference in their entirety into this disclosure.

Present day commercial dry adhesion tapes using the Gecko tape, by way of example Geckskin® super adhesive nanotape, leave no residue on the footwear surface when removed.

The commercial artificial nanotape is modeled after the feet of the Tokay gecko animal known to climb vertical surfaces and even cling to ceilings using nanometer sized keratin hairs on the bottom pads of the feet bunched in large numbers. Microscopy techniques found that the Tokay gecko's toe pads each having ≈20 rows of sticky lamellae, each lamella with many seta arrays consisting of thousands of setae, with ≈200,000 seta per toe, each seta consisting of hundreds to 1,000 spatulae at its end.

Studies confirm an intermolecular phenomenon known as van der Waals force are exerted by each of these hairs strong enough when large bunches of nanometer sized hair are pressed from a roughly straight position to a bent position. The gecko moves to release the bent hair by pressing forward to return the hairs to a roughly straight position. These minute hairs are grouped as feet pads and referred to as seta. The hairs are in pods of seta, with the hairs numbering in the hundreds of thousands per pod, generating the gecko's holding force.

The gecko discovery ascertained that the van der Waals effect was the dominant force explaining the dry adhesion force multiplied by the vast number of seta hairs. A relatively mild force forward and somewhat upward push acts as the animals release mechanism from bent to straight hairs on the bottom of the gecko feet pads. Moisture and temperature (cold) was found to have little effect on the holding power of the Geckskin nanotape.

A recent breakthrough in making artificial materials for gecko tape is disclosed in an article from New:Scientist by Will Knight dated 1 Jun. 2003. He reported that Andre Geim and research colleagues at the UK's Manchester University in a web article entitled: "Gecko tape will stick you to ceiling", announced artificial creation of a tape having millions of hairs to collectively produce a powerful adhesive effect. Individual hairs are 0.2 microns in diameter—the same as gecko hairs. The citation is newscientist.com/article/dn3785-gecko-tape-will-stick-you-to-ceiling. This article is incorporated in total by reference in this disclosure.

Researchers found that the Geckskin tape's artificial hairs had to be soft and flexible enough to attach to uneven surfaces and further that the substrate the hairs were mounted on also had to be sufficiently flexible for the material to work. Flexibility of both compensates for unevenness or dusty surfaces.

Figure 3:
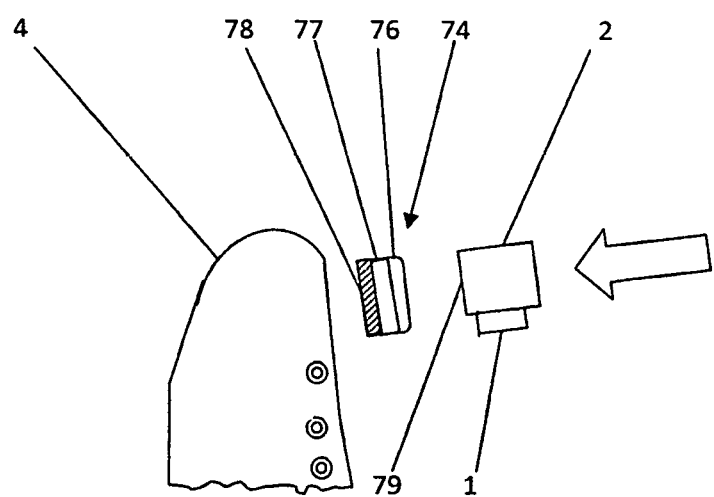
FIG. 3 is a partial side view of the footwear front toe tilted with the tip of the toe facing upward to have "Gecko" tape pressed between the sensor holder and the front toe

FIG. 3 is a view of the athlete's footwear 4 with the Gecko tape 74 placed between the undersurface 79 of the sensor holder 2 and the top surface of the toe area of the footwear.

The layers making up the Gecko tape are depicted in the FIG. 3 detail wherein layer 78 is the dry adhesive setae (hair). Layer 77 is a flexible substrate on which the hairs are mounted. Layer 76 is the bonding adhesive for sticking the layer 77 to the holder undersurface 79.

When pressed together the adhesive layer 76 holds the tape 74 to the underside of the sensor holder with motion sensor 1 inserted therein. The flexible intermediate substrate 77 mounts the artificial pods of seta hair 78 which are pressed and bent down to hold to the footwear's toe area and pressed sideways to release the holding force of the hair.

This invention discloses a factory installed generically developed calibration factor which is easily replaced by a customized calibration factor to extremely accurately measure the jump heights of the individual athlete. The athlete has the choice of the external Vertec® direct jump height device or the preferred external high speed video camera(s) of a 5G smartphone for the "Absolute" external jump height reference. 5G or higher refers to rate of data transmission. Examples of 5G smartphones include the Apple® iPhone 10 iOS or 11 iOS or higher (such as the recent iPhone 13 series) having Bluetooth protocol 4.0 or higher with BLE. Other equivalent 5G operating systems such as the 5G Android® operating systems may also be used. When determining the high speed video calibration, smartphones having 5G connectivity are preferred as more accurate and faster data points are recorded. Other examples of 5G connectivity smartphones are the Huawei Mate 30 Pro EG, the Samsong Galaxy S10 smartphone and the Motorola Moto Z3 add on.

Other systems adaptable, such as WiFi can also be used. It is recommended that the mobile smart computer device chosen have a high speed video camera with a slow motion 240 frames per second speed or higher. By higher is specifically meant, but not limited to, 5G smartphones and to a lesser extent sub 6/5G as well as millimeter 5G. The preferred mobile smart computer devices are the Samsung Galaxy smartphone series (S20, S20+, S20 Ultra or S21, S21+ and S21Ultra). These lines uses 5G connectivity and major camera upgrades featuring a slow motion of 240 fps switchable to a super slow motion mode of 960 fps when using the S20 Ultra.

When it comes to shooting slow-motion video the Samsung recently released Galaxy S21, S21+ can both deliver 960 fps when shooting slow motion video BUT the S21 Ultra (the most expensive) cannot record at this speed while still being able to produce 960 fps output. Instead the flagship model records at 480 fps and then uses software-based enhancement to produce 960 fps output. The discrepancy, revealed in a footnote on Samsung's Galaxy S21 comparison page, reads: "On Galaxy S21 5G and S21+5G, users can record approximately 0.5 seconds of video captured at 960 fps with approximately 16 seconds of playback. On Galaxy S21 Ultra 5G, users can record approximately 1 second of video captured at 480 fps and digitally enhance the video to 960 fps with approximately 32 seconds of playback."

Samsung has identified that the new 108-megapixel Isocell HM3 main camera sensor is responsible causing a slower shutter speed than those found in the smaller S21 models.

The S21, S21+ and S21 Ultra further feature a 100× zoom compared to the 30× zoom of the S20+ and 3× zoom of the S20.

Additionally, the S21, S21+ and S21 Ultra support a Super-Wide Video option having high resolution 100× zoom feature Zoom-In mode. The above features enable crystal clear close up viewing of camera recordings of the body posture of the jumper with the Zoom-In option available for recording details of jump movement of various body parts such as hands, feet, legs, knees, arms, head and torso available for comparison using computer tools such as Augmented Reality (AR) algorithms and algorithm apps as the comparison model. Also, this feature enables rapid viewing of bad form to be quickly analyzed in real game time situations as this may indicate among other things, a possible injury is affecting the athlete's performance.

The Samsung S21 Ultra 5G smartphone is the preferred smartphone of choice as overall the latest features include Scene Optimization to sense and adjust brightness level using night Mode. Only, the S21 Ultra has two telephoto lens camera(s) which with an aperture of f/1.8 and 100× Space Zoom provides for a resolution of 3200×1400 allowing a frame refresh rate at 120 Hz to depict 1440 pixel resolution. Additionally, the wide screen mode has the 108 megapixel sensors enhanced by a laser autofocus called a PDAF (phase-detection autofocus) to assist the auto focus. The ultra-wide screen mode has an aperture of f/2.2 with a 120 degree FOV with a DPAF (Dual-Pixel Auto Focus).

The S21 Ultra has a zoom range from 10× to 100× with image quality boosted by powerful Super Resolution AI (Artificial Intelligence). Up to 20 frames are captured and processed at near instantaneous speeds. The telephoto cameras, in Zoom Lock mode, when shooting at high magnification uses intelligent software to set the image in place with minimal shake.

The S21 Ultra's Scene Optimizer mode enhances the video frames to increase scene clarity with over 30 scenes to select from including PEOPLE and SHOES. The S21 Ultra's Scene Optimizer (not considered an overlay) is programmed to recognize, among which scenes include PEOPLE and SHOES are being videoed. The present invention additionally uses Augmented Reality algorithms to introduce a Grid Measurement Screen Overlay over the actual video frames. The viewer quickly and accurately uses these to measure height of the jump.

An example of an augmented reality measuring length tool is the AirMeasure® app developed by Laan labs for the Apple iOS® operating system. Similar apps are available for Android operating systems such as used by Samsung Galaxy smartphones.

The principles disclosed herein have broader application in the art of measuring jumping than just a standing vertical jump which is also referred to as the standing broad jump or standing long jump or broad jump (terms used for tests by athletic combines such as the NFL Combines). With adjustments for anatomies of animals (paws or hoofs) this invention is easily adaptable by trainers in the racing industry. Hence the term "athlete" is generic as used and refers to the human species as an example of type of athlete but is not intended to be limited solely thereto.

The pairing of a mems sensor with a smartphone with advanced video modes is generally well known. In this invention, in the step of reviewing the record of video frames for height determination, the reviewing athlete is expected to throw out jump heights where excessive knee bending and/or arm swinging movement are detected. Other no-no's, such as use of footwear having spring heels, wearing sandals, shoes on wrong foot, shoe size too small/large, gum on foot sole, foot laces untied, wearing no socks, wearing gang colors, not wearing name brand footwear, etc, are also easily picked up by the Zoom-In mode filming at camera 100× magnification.

SUMMARY

Figure 1A:
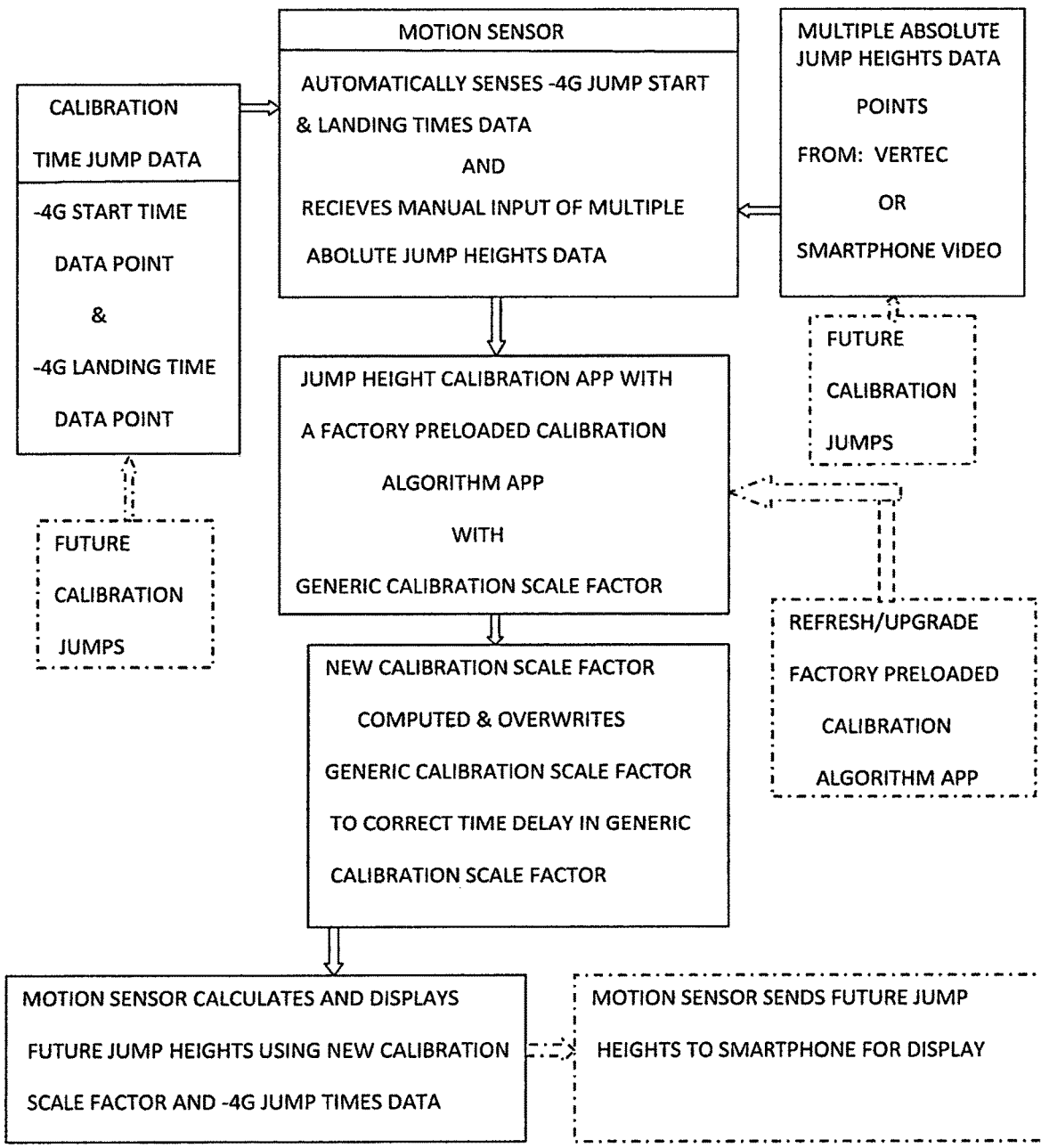
FIG. 1A is a flow chart of the interface between the motion sensor and jump data used to modify/overwrite a generic calibration scale factor of a factory preloaded calibration algorithm app installed in the motion sensor.

Referring to the flow chart of FIG. 1A, the athlete has the option depending on available equipment to use the method of external Vertec calibration or the preferred method of external video calibration. In addition, the externally verified actual jump heights permit feedback to further refine the accuracy of the generic scale factor with each athlete using the above outlined methods. The big data feedback of verifiable jump data permits real time leveraging of the accuracy of the constantly upgraded factory calibration scale factor. This feedback is automatically re-introduced (freshened) in the JAWKU® vertical motion sensor as a new over-write of the existing personalized calibration scale factor enabling or eliminating the need for new calibration jumps by the athlete to maintain cutting edge competitive accuracy desirable in the mastery of new jumping exercises and skills.

In essence, the invention provides for a continuously growing data pool evolving a more accurate factory loaded calibration scale factor. The athlete retains the option of entering the calibration jump height data as a final calibration refinement over-write. The ongoing feedback from an ever growing population of jumpers using the sensed vertical motion sensor −4 g takeoff and −4 g landing times combined with the average jump height ("ABSOLUTE" reference height) captured by the super-slow motion video of the several jump heights achieves the high accuracy data measurement objectives of the present invention.

Once the sensor is recalibrated with the customized scale factor, the athlete only uses the toe mounted motion sensor to measure any future jump heights.

The novel use of the gecko tape to interlock the sensor holder to the shoe with the gecko tape only on the sensor holder provides ultimate comfort to the toes of the wearer of the shoe while at the same time not marring the shoe's appearance when removed, an important marketing tool.

What is claimed is:

1. A method of recalibration by an athlete of a motion sensor which measures jump heights having a preinstalled generic factory scale calibration factor with a new calibration scale factor by the athlete wearing footwear mounting the motion sensor over the toes of the athlete, the athlete activating the motion sensor to detect jump start and jump finish times of a −4 g start and a −4 g landing and then automatically send the jump start and finish times to a jump height algorithm app in the motion sensor using the preinstalled generic factory scale calibration factor which introduces a time delay for the jump having a "raw" delta T (Time); and the athlete removing the time delay by inputting to the motion sensor several measurements of jump heights as measured from an external direct jump height device which measurements are taken contemporaneously with the detection of the jump start and finish times causing the jump height algorithm app to rewrite and override the preinstalled generic factory scale calibration factor with the new calibration scale factor customized to the athlete.

2. The method of claim 1 wherein a jumping movement by the athlete activates the external direct jump height device.

3. The method of claim 2 wherein the athlete selects as the external direct height device a direct height jump device having a row of markers vertically spaced and each marked with a jump height acting as an "absolute" height jump reference and the athlete jumps to reach and touch the highest marker to obtain the measurements of each jump.

4. The method of claim 1 wherein the jump height app calculates the jump height using the new calibration scale factor.

5. The method of claim 1 wherein the athlete selects as the direct jump height device a smartphone or other mobile smart computer device having at least one video camera with slow motion or super slow motion fps (frame per second) video recording modes, the athlete positions the video camera near the athlete to trigger selected film recording modes commencing on the motion of the jump triggering film recording for 4 seconds and performs several jumps each of which are video recorded to capture video frames measuring the highest jump heights, the athlete reviews the video jump frames and inputs the several measurements of jump heights to the motion sensor.

6. The method of claim 5 wherein the selected video recording modes are in a slow motion or super slow motion range of 240 fps up to at least 960 fps.

7. The method of claim 5 wherein the athlete's review of the video jump frames to determine measurements of jump heights are of video jump frames coinciding with the highest height filmed in the time frame defined by the start and finish times sensed by the motion sensor for each of the several jumps.

8. The method of claim 5 further including the athlete computing an average height ($H_{video}$) representing an average jump height unique to the athlete and inputs this average height to the motion sensor.

9. The method of claim 8 wherein the athlete uses the jump height algorithm app to determine the "true" delta T time recorded on the video tape taken in slow motion by the camera of the smartphone or other mobile smart computer device and reviewed by the athlete to compute an average height ($H_{video}$) representing an average jump height unique to the athlete.

10. The method of claim 5 comprising the step of the athlete reviewing the video jump frames with the the aid of an augmented reality overlay screen app superimposed over the video frames and optionally the aid of a S21 Ultra Scene Optimizer®.

11. The method of claim 5 wherein the motion sensor upon being inputted with the several measurements of jump heights causes the jump height algorithm app to calculate a unique to the athlete "true" calibration scale factor used to replace the generic preloaded calibration scale factor.

12. The method of claim 5 wherein the at least one smartphone or other mobile smart computer device is selected by the athlete to have one of an operating system of: an Apple 11® iOS or higher, a Huawei Mate 30 Pro EG® using an Android® operating system,
  a Samsung Galaxy® S10 Android® operating system or higher series Samsung Galaxy® S20 5G, S20+5G, S20 Ultra 5G, S21 5G, S21+5G or S21 Ultra 5G, or a Motorola® Moto Z3 Android® add on operating system.

13. The method of claim 12 wherein the athlete when using the Samsung Galaxy S21 Ultra 5G operating system uses 480 fps super slow motion mode having a software enhancement built into the camera to film the equivalent of 960 fps at super slow motion frame rate.

14. A motion sensor for measuring jump heights of an athlete wherein the improvement comprising the motion sensor having six degrees of freedom sensors which automatically sense time jump data of a jump start time and a jump landing time, the motion sensor further having apps to determine which time jump data represents a −4 g start time and a −4 g landing time, the motion sensor further having a factory preloaded calibration algorithm app having a generic calibration scale factor, the motion sensor further having a motion sensor jump height app which computes a new calibration scale factor based on actual "absolute" jump heights taken by the athlete, the new calibration scale factor overwriting the generic calibration scale factor whereby the motion sensor is customized for measuring with great accuracy the jump heights of the athlete.

15. The motion sensor of claim 14 wherein the new calibration scale factor is upgradable by input of new data unique to the athlete and the generic calibration scale factor is upgradeable by input of new jump data derived from multiple athletes.

* * * * *